US006288138B1

(12) United States Patent
Yamamoto et al.

(10) Patent No.: US 6,288,138 B1
(45) Date of Patent: Sep. 11, 2001

(54) DENTAL ADHESIVE KIT

(75) Inventors: Takashi Yamamoto; Masami Arata; Hideyuki Ueki; Harumi Tanaka; Tamotsu Tomikawa; Haruka Otsuki, all of Moriyama (JP)

(73) Assignee: Sun Medical Co., Ltd., Moriyama (JP)

( * ) Notice: Subject to any disclaimer, the term of this patent is extended or adjusted under 35 U.S.C. 154(b) by 0 days.

(21) Appl. No.: 09/213,175

(22) Filed: Dec. 17, 1998

(30) Foreign Application Priority Data

Dec. 18, 1997 (JP) ..................................... 9-349143

(51) Int. Cl.$^7$ ............................ A61K 6/083; C08L 43/00; C08L 41/00; C09J 133/02; C08J 3/28
(52) U.S. Cl. ........................ 523/118; 523/116; 524/547; 524/556; 524/560; 524/100; 524/832; 522/17; 522/20; 526/277
(58) Field of Search ..................................... 523/118, 116; 524/547, 556, 560, 100, 832; 522/17, 20; 526/277

(56) References Cited

U.S. PATENT DOCUMENTS

| | | | |
|---|---|---|---|
| 5,171,149 | * | 12/1992 | Alpert . |
| 5,288,341 | * | 2/1994 | Kojima et al. ................ 156/316 |
| 5,530,038 | * | 6/1996 | Yamamoto et al. . |
| 5,670,657 | * | 9/1997 | Kojima et al. ................ 549/39 |
| 5,834,532 | | 11/1998 | Yamamoto et al. . |

FOREIGN PATENT DOCUMENTS

| | | |
|---|---|---|
| 56-120610 | 9/1981 | (JP) . |
| 63-25562 | 5/1988 | (JP) . |
| 662688 | 8/1994 | (JP) . |
| 72613 | 1/1995 | (JP) . |
| 10245525 | 9/1998 | (JP) . |

OTHER PUBLICATIONS

Grant & Hackh's Chemical Dictionary, 5th Edition Mcgraw–Hill, N.Y p. 299 1987.*

* cited by examiner

Primary Examiner—Peter A. Szekely

(57) ABSTRACT

A kit for dental adhesive comprising a radical polymerizable monomer having an acid group in the molecule, a photosensitizer and/or a peroxide, a water-soluble organic solvent, an organic sulfinic acid and/or a salt thereof or a barbituric acid and/or a derivative thereof, and water. The kit may further comprises a radical polymerizable monomer which has no acid group and is insoluble or hardly soluble in water, an amine compound, a silane coupling agent and a 1,3,5-triazine-2,4-dithion derivative. By using this kit, the adhesive composition can be applied directly to a dentine without conducting a pretreatment.

19 Claims, No Drawings

DENTAL ADHESIVE KIT

FIELD OF THE INVENTION

The present invention relates to a kit for a dental adhesive. More specifically, it relates to a kit for a dental adhesive (an adhesive composition) which is excellent in curability at a temperature range and a humidity/wet range which affect living bodies as well as the water resistance, strength, adhesion, color tone and storage stability of a cured product. Further more specifically, it relates to a dental adhesive kit for a curable adhesive composition for use as a coating material, bonding material, primer or pre-treatment agent which can be applied not only to a tooth but also to dental metals, ceramics and resins such as composite resins, hard resins, resins for a base and cement, particularly a curable adhesive composition having excellent performance in an adhesive material or coating material application out of these application fields.

PRIOR ART

Heretofore, as a curable composition to be applied to a dental adhesive material, composite resin, hard resin, floor resin, cement or coating material, there have been proposed many curable compositions which comprise a radical polymerizable monomer such as a vinyl monomer typified by a styrene derivative and (meth)acrylic acid derivative and a polymerization initiator (catalyst or curing agent in some cases) for polymerizing the monomer to cure.

Requirements for a curable composition for a living body, especially a tooth, include a relatively high curing speed at a temperature range and a humidity/wet range to which a living body can be exposed to, a controllability of the curing speed, the high water resistance, strength and adhesion of a cured product, an easy controllability of color tone, and excellent storage stability that the composition can be preserved while retaining these properties stably. When the curable composition is used as an adhesive material, materials to be bonded with this composition include not only teeth but also a variety of materials such as metals, ceramics, resins before and after curing (may be simply referred to as "resin" hereinafter), composite resins, resin cement and the like. Therefore, the curable composition must have properties for bonding these materials.

There are the following proposals for attaining the above requirements using a curable composition comprising a radical polymerizable monomer and a photopolymerization initiator. JP-B 53-33687 and JP-B 54-10986 (the term "JP-B" as used herein means an "examined Japanese patent publication") propose a composition comprising a carbonyl compound such as α-diketone and an amine. However, the cured product thereof changes its color tone and is unsatisfactory in terms of water resistance, strength and adhesion. JP-A 56-120610 (the term "JP-A" as used herein means an "unexamined published Japanese patent application") proposes a photocurable composition comprising a vinyl monomer having an acid group, α-diketone and an aromatic sulfinate. The composition is excellent in the stability of color tone but has problems with strength and adhesion durability. JP-B 61-3684 proposes a composition comprising a monomer containing carboxylic anhydride, an organic peroxide, amine and aromatic sulfinate but the composition is unsatisfactory in terms of adhesion strength. JP-A 60-44508, JP-A 60-123515 and JP-B 7-2613 propose compositions each of which comprises a carboxylic acid-containing monomer and an aromatic sulfinate and further contains an amine or α-diketone and dialdehyde according to application purpose. These compositions, too, do not have sufficiently high adhesion strength. Thereafter, JP-B 6-62688 proposes a composition which comprises a carboxylic acid-containing monomer, α-diketone, amine and aromatic sulfinate and has greatly improved color tone stability and improved adhesion and durability.

The above proposals are based on the premise that the surface of a tooth is in advance treated with an etching composition containing an acidic compound. This etching is aimed to remove a chippings layer (smear layer) remaining on the tooth surface when the tooth is chipped, and to improve adhesion strength. In recent years, there has also been proposed a method for treating the surface of a tooth with a primer composition comprising a monomer after it is etched or while the smear layer remains thereon, and then applying a curable composition thereto. The proposals for improving adhesion strength by applying the curable composition after etching or treating with a primer involve such a problem that it takes an operator much time and labor and becomes complicated, thereby extending treatment time and increasing a load on a patient.

It is generally considered that an adhesive material component must be diffused up to a healthy tooth and the diffused adhesive material component must be cured without fail so as to be firmly bonded to the tooth for a long time. However, various problems have been apprehended for a curable adhesive composition which is applied after the use of an etching composition and a primer composition, or an adhesive material which is applied in the same manner. For example, in a method comprising use of a tooth etching material and a curable composition, even a healthy tooth may be invaded by etching for removing a smear layer which is formed when dental caries is chipped and removed, thereby causing deterioration in a bonded site.

It is desired that an adhesive material for teeth should firmly bond a repair material to a tooth without a gap and the treatment should be done in a short period of time with ease as much as possible because this bonding work is carried out in a mouth.

As means of treating the surface of a tooth to firmly bond a resin repair material to the tooth, the following three methods are mainly employed. That is, the first means is an etching method comprising applying a solution having tooth-deliming properties such as phosphoric acid or citric acid to the surface of enamel and/or dentine and washing it with water, the second means is an etching primer method comprising applying a primer to the surface of a tooth which has been subjected to the above etching method and drying it, and the third means is a self-etching primer method comprising applying a primer having a deliming function to a tooth, without etching. These tooth treating methods are a pretreatment which is conducted before an adhesive material for bonding a material for repairing a partially lost tooth to a tooth, that is, a bonding material or resin cement, is applied to a tooth. The tooth and the material for filling up the loss cannot be firmly bonded to each other with the pre-treating composition alone.

JP-B 63-25562 discloses a dental material comprising a vinyl monomer having an acid group, α-diketone, aromatic sulfinate or thiourea.

JP-A 10-245525 discloses an adhesive composition which comprises a specific phosphoric acid group-containing polymerizable monomer, a polycarboxylic acid group-containing polymerizable monomer and a polymerization initiator and does not require a retreatment for a tooth.

SUMMARY OF THE INVENTION

It is an object of the present invention to provide a kit for a dental adhesive (an adhesive composition) having sufficient adhesion performance to dentine and sufficient durability.

It is another object, of the present invention to provide a kit for a dental adhesive composition which eliminates the need for carrying out a pretreatment such as etching and primer treatment before a curable composition is applied to a tooth, particularly an adhesive composition which can be directly applied to a tooth from which dental caries has been chipped and removed (i.e., a healthy tooth having a smear layer).

Stated more specifically, the present invention provides a kit for a dental adhesive composition (may be referred to as "self-etching bonding material composition" hereinafter) which is directly contacted with a tooth to delime part or all of the smear layer in order to diffuse into the substrate of the tooth an adhesive material component exhibiting adhesive strength and at the same time, forming a coating having a required thickness on the surface of the tooth. The composition can be most advantageously applied to a tooth which is not subjected to a pretreatment as well as a tooth which has been etched and/or applied with a primer depending upon circumstances.

It is a further object of the present invention to provide a kit which can preserve the adhesive composition of the present invention stably for a long time.

Other objects and advantages of the present invention will become apparent from the following description.

According to the present invention, firstly, the above objects and advantages of the present invention are attained by a kit for a dental adhesive comprising:

(A) a radical polymerizable monomer having an acid group in the molecule, (C) a photo sensitizer (C1) and/or a peroxide (C2), (D) a water-soluble organic solvent, (E) an organic sulfinic acid and/or a salt thereof, or a barbituric acid and/or a derivative thereof, and (F) water, wherein at least the component (E) is impregnated into an applicator and other components not impregnated in the applicator are contained in at least one vessel and are brought into contact with and mixed with the component (E) impregnated in the applicator right before use.

Secondly, the above objects and advantages of the present invention are attained by a kit for the above dental adhesive which further comprises (B) a radical polymerizable monomer which has no acid group and is insoluble or hardly soluble in water.

The composition of the present invention may contain as optional components at least one compound selected from the group consisting of:

(G) an amine compound, (H) a silane coupling agent, and (I) a 1,3,5-triazine-2,4-dithion derivative, in addition to the above components (A) to (F).

A large amount of water exists in the tissue of a tooth, especially dentine. It is said that an adhesive material component must be sufficiently diffused into the tissue and cured in order to develop sufficient adhesion by applying an adhesive material to the tissue. It has been revealed that when an adhesive material having excellent adhesion performance is used, a resin-impregnated layer in which both the tissue of a tooth and an adhesive material component are existent is formed near the interface between the tooth and the adhesive. It is generally said that it is preferred to use a polymerizable monomer which is easily mixed with water contained in the tissue of a tooth or a polymerization initiator to diffuse an adhesive material component into the tissue of the tooth. Though high adhesion strength can be obtained in a short period of time with this method, long-term adhesion durability is low, which is assumed to be caused by a reduction in water resistance due to the use of a component which is easily soluble in water. As proposed by JP-B 6-62688, there is a composition comprising a water-soluble volatile organic solvent such as ethanol but it cannot be said that the composition exhibits sufficient adhesion performance. This is probably because water contained in the tissue of a tooth Is not well substituted by the proposed composition well.

The inventors of the present invention have conducted studies to improve adhesion, and have accomplished the present invention by reducing pH by promoting the isolation of protons derived from a polymerizable monomer containing an acid group in the presence of water, dissolving the water-insoluble polymerizable monomer in an organic solvent which can be mixed with water in a desired ratio and containing water in limits that do not cause phase separation before the polymerizable monomer is applied. The following adhesion mechanism is conceivable from the components and their composition of the present invention. That is, when the composition of the present invention is brought into contact with the surface of a tooth, hydroxyapatite contained in a smear layer existent on the surface of the tooth is first dissolved by the composition having a low pH to promote the diffusion of the components of the composition into a healthy tooth, and secondly, at the same time, an organic solvent contained in the composition is mixed with water contained in the tooth so that water contained in the tissue of the tooth and the composition of the present invention are mixed swiftly near the contact interface. Thirdly, water is partially evaporated along with the gradual evaporation of the organic solvent, water is removed from the adhesive interface little by little, and the radical polymerizable monomer enters into the detail of the tissue of the tooth little by little and is adsorbed. It is considered that in the initial three stages, the radical polymerizable monomer having an acid group or/and carboxylic anhydride in the molecule is adsorbed with priority. Subsequently, since the evaporation speed of the organic solvent is faster over that of water and when the proportion of the organic solvent contained in the composition exceeds a certain value, the polymerizable monomer which is not mixed with water is formed as extremely small oil drops in the composition, the composition becomes an opaque liquid. At this point, it is assumed that the radical polymerizable monomer having an acid group or/and carboxylic anhydride in the molecule functions as a surfactant and is in a microscopically phase separation state. Further, as the evaporation of the solvent proceeds, the adsorption of the radical polymerizable monomer to the tissue of the tooth proceeds so that the oil drops are gradually adsorbed to the surface of the tooth to remove water from the adhesive interface, and the wetted surface of the tooth is substituted by a composition comprising a radical polymerizable monomer having water resistance and a polymerization initiator. Then, by applying compressed air or hot air to a site applied with the composition, water and the organic solvent not required for bonding are evaporated. At this point the organic solvent plays an important role to allow the adhesive material component on the surface to hold a thickness enough to exhibit adhesion strength. Thereafter, the component is cured through exposure to visible radiation and then a repair material such as a composite resin is applied to complete a treatment. Thus, while water present near the adhesive interface is gradually removed to the outside of the tissue by the composition of the present invention containing the organic solvent, the curable composition is deeply infiltrated into the tissue of the tooth and an effective coating thickness is ensured to obtain high adhesion strength even under wet conditions and form a water insoluble or hardly soluble cured product. Thus, excellent water resistance can be obtained.

In the present invention, the component (A) is a radical polymerizable monomer having an acid group or an acid base in the molecule. Illustrative examples of the acid group include a carboxylic acid group, carboxylic anhydride group, phosphoric acid group and sulfonic acid group.

Monofunctional polymerizable monomers having a carboxylic acid group or carboxylic anhydride group in the molecule are, for example, monocarboxylic acids, dicarboxylic acids, tricarboxylic acids, tetracarboxylic acids, polycarboxylic acids and anhydrides thereof. Compounds usable in the present invention are carboxylic acids and/or anhydrides thereof cited in JP-B 6-62688. The compounds include, for example, (meth)acrylic acid, maleic acid, p-vinylbenzoic acid, 11-(meth)acryloyloxy-1,1-undecanedicarboxylic acid (MAC-10), 1,4-di(meth)acryloyloxyethylpyromellitic acid, 6-(meth)acryloyloxyethylnaphthalene-1,2,6-tricarboxylic acid, 4-(meth)acryloyloxymethyltrimellitic acid and an anhydride thereof, 4-(meth)acryloyloxyethyltrimellitic acid and an anhydride thereof, 4-(meth)acryloyloxybutyltrimellitic acid and an anhydride thereof, 4-[2-hydroxy-3-(meth)acryloyloxy]butyltrimellitic acid and an anhydride thereof, 2,3-bis(3,4-dicarboxybenzoyloxy)propyl (meth)acrylate, 2-, 3- or 4-(meth)acryloyloxybenzoic acid, N,O-di(meth)acryloyloxytyrosine, O-(meth)acryloyloxytyrosine, N-(meth)acryloyloxytyrosine, N-(meth)acryloyloxyphenylalanine, N-(meth)acryloyl-p-aminobenzoic acid, N-(meth)acryloyl-O-aminobenzoic acid, adduct of glycidyl (meth)acrylate with N-phenylglycine or N-tolylglycine, 4-[(2-hydroxy-3-(meth)acryloyloxypropyl)amino]phthalic acid, 3- or 4-[N-methyl-N-(2-hydroxy-3-(meth)acryloyloxypropyl)amino]phthalic acid, (meth)acryloylaminosalicylic acid and (meth)acryloyloxysalicylic acid. Out of these, 11-methacryloyloxy-1,1-undecanedicarboxylic acid (MAC-10) and 4-methacryloyloxyethyltrimellitic acid (4-MET) or an anhydride (4-META) thereof are preferred. Polyfunctional polymerizable monomers having at least two carboxyl groups in the molecule and usable as the component (A) are dicarboxylic acids, tricarboxylic acids, tetracarboxylic acids and derivatives thereof, as exemplified by an addition product of 2-hydroxyethyl (meth)acrylate and pyromellitic dianhydride (PMDM), addition reaction product of 2 moles of 2-hydroxyethyl (meth)acrylate and 1 mole of maleic anhydride or 3,3',4,4'-benzophenone tetracarboxylic dianhydride (BTDA) or 3,3',4,4'-biphenyltetracarboxylic dianhydride, and 2-(3,4-dicarboxybenzoyloxy)1,3-di(meth)acryloyloxypropane.

Polymerizable monomers having at least one phosphoric acid group in the molecule include, for example, 2-(meth)acryloyloxyethylacid phosphate, 2- and 3-(meth)acryloyloxypropylacid phosphate, 4-(meth)acryloyloxybutylacid phosphate, 6-(meth)acryloyloxyhexylacid phosphate, 8-(meth)acryloyloxyoctylacid phosphate, 10-(meth)acryloyloxydecylacid phosphate, 12-(meth)acryloyloxydodecylacid phosphate, bis{2-(meth)acryloyloxyethyl}acid phosphate, bis(2 or 3-(meth)acryloyloxypropyl)acid phosphate, 2-(meth)acryloyloxyethylphenylacid phosphate, 2-(meth)acryloyloxyethyl p-methoxyphenylacid phosphate and the like. The phosphoric acid group in these compounds may be substituted by a thiophosphoric acid group. Compounds disclosed by JP-A 54-21438, JP-A 59-140276 and JP-A 59-142268 may be used as the polymerizable monomer having a thiophosphoric acid group. The following compounds are examples of the polymerizable monomer having a thiophosphoric acid group and may be tautomeric materials shown in brackets.

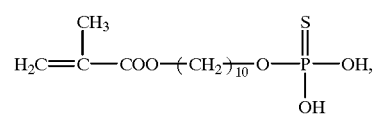

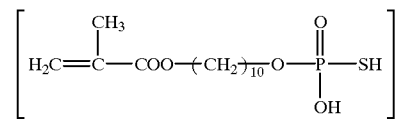

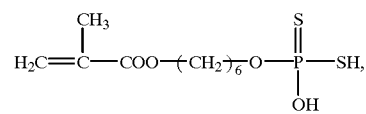

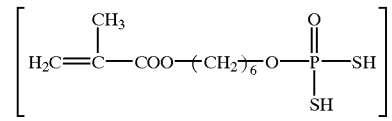

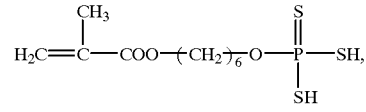

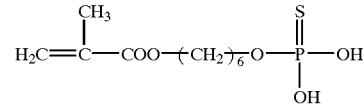

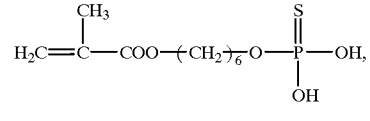

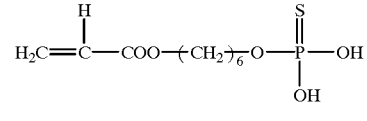

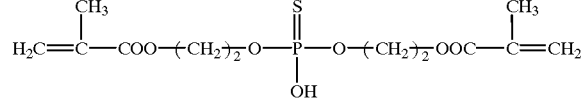

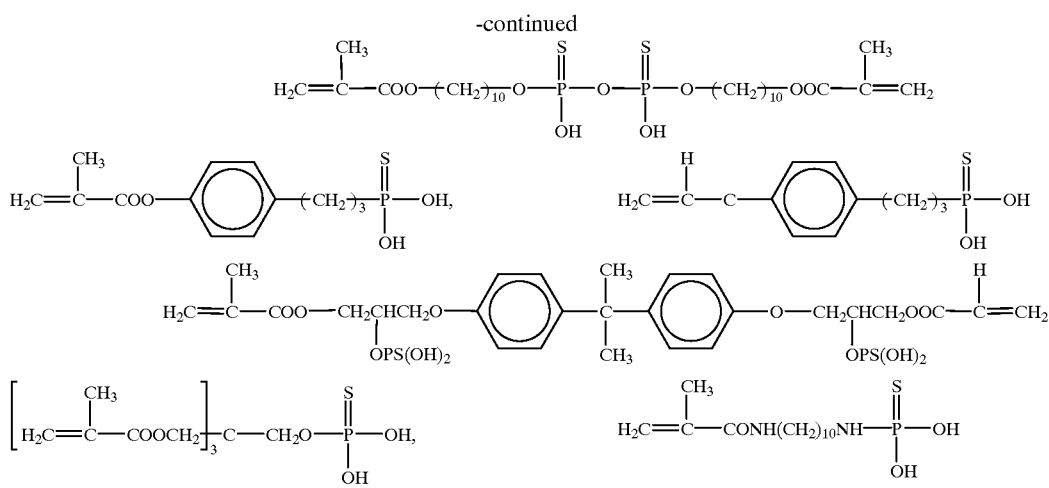

Of these, 2-(meth)acryloyloxyethylphenylacid phosphate and 10-(meth)acryloyloxydecylacid phosphate are preferred. These polymerizable monomers having a phosphoric acid group may be used alone or in combination.

Polymerizable monomers having a sulfonic acid group in the molecule include, for example, 2-sulfoethyl (meth) acrylate, 2- or 1-sulfo-1 or 2-propyl (meth)acrylate, 1- or 3-sulfo-2-butyl (meth)acrylate, 3-bromo-2-sulfo-2-propyl (meth)acrylate, 3-methoxy-1-sulfo-2-propyl (meth)acrylate, 1,1-dimethyl-2-sulfoethyl (meth)acrylamide and 2-methyl-2-(meth)acrylamlde propanesulfonic acid. Of these, 2-methyl-2-(meth)acrylamide propanesulfonic acid is preferred.

The component (A) may be a polymerizable monomer part or all of the acid groups of which is substituted by a salt such as a monovalent or polyvalent metal salt or ammonium salt. In this case, it is desirable that the component (A) functions as an acid when it is used in conjunction with other acidic compound and contacted to the other acidic compound.

The above components (A) may be used alone or in combination.

The component (B) of the present invention is a radical polymerizable monomer having no acid group other than the component (A) which is insoluble or hardly soluble in water. The polymerizable monomer is specified as a polymerizable monomer whose phase separation is seen with the naked eye (or it is not dissolved) when it is added to distilled water to a concentration of 5 wt % and shaken at 37° C. for 10 minutes. That is, the polymerizable monomer has normally a solubility at 37° C. of 5 wt % or less. Specific examples of the polymerizable monomer include aromatic vinyl compounds such as styrene and divinyl benzene; vinyl esters such as vinyl acetate; aliphatic esters of (meth)acrylic acid such as methyl (meth)acrylate, ethyl (meth)acrylate, propyl (meth)acrylate, butyl (meth)acrylate, pentyl (meth)acrylate, hexyl (meth)acrylate, neopentyl glycol di(meth)acrylate and trimethylolpropane tri(meth)acrylate; aromatic esters such as phenyl (meth)acrylate; aromatic (meth)acrylates such as 2-hydroxy-3-phenoxypropyl (meth)acrylate, adduct of 1 with 2 moles of glycidyl methacrylate mole of bisphenol A (Bis-GMA), condensate of 1 mole of an addition polymer of bisphenol A with glycidyl ether and 2 moles of (meth)acrylic acid (VR90) and condensate of 1 mole of an adduct of bisphenol A with ethylene oxide and 2 moles of (meth) acrylic acid (number of addition chains of ethylene oxide m+n≧2; m+n=2.6 is abbreviated as 2.6E); urethane bond containing (meth)acrylates typified by 2-(meth) acryloyloxyethyl isocyanate and an adduct (uDMA) of 2 moles of 2-hydroxyethyl (meth)acrylate with 1 mole of 2,2,4-(or 2,4,4-)trimethyl-1,6-hexamethylene diisocyanate; aliphatic esters of (meth)acrylic acid such as 1,6-hexamethylene dimethacrylate (1,6-HX), neopentyl glycol di(meth)acrylate and trimethylolpropane tri(meth)acrylate; polyethylene glycol di(meth)acrylates (number of chains n=less than 6) such as ethylene glycol di(meth)acrylate, diethylene glycol di(meth)acrylate and triethylene glycol di(meth)acrylate; and polypropylene glycol di(meth) acrylates (number of chains n=12 or less) such as propylene glycol di(meth)acrylate, dipropylene glycol di(meth) acrylate, tripropylene glycol di(meth)acrylate and nonapropylene glycol di(meth)acrylate.

The component (C) of the present invention is photosensitizer (C1) and/or a peroxide (C2). The photo-sensitizer is excited by light alone or in the co-presence of other compound and functions to cure the curable composition of the present invention. The photosensitizer is, for example, (c11) an α-ketocarbonyl compound or (c12) acylphosphine oxide compound. Specific examples of the component (c11) are α-diketone, α-ketoaldehyde, α-ketocarboxylic acid, α-ketocarboxylate and the like. More specifically, examples of the compound (c11) include α-diketones such as diacetyl, 2,3-penta-di-one, 2,3-hexadione, benzyl, 4,4'-dimethoxybenzyl, 4,4'-diethoxybenzyl, 4,4'-oxybenzyl, 4,4'-dichlorobenzyl, 4-nitrobenzyl, α-naphthyl, β-naphthyl, camphorquionone, camphorquinonesulfonic acid, camphorquinonecarboxylic acid and 1,2-cyclohxanedione; α-ketoaldehydes such as methylglyoxal and phenylglyoxal; and others such as pyruvic acid, benzoylformic acid, phenylpyruvic acid, methyl pyruvate, ethyl benzoylformate, methyl phenylpyruvate and butyl phenylpyruvicate. Of these α-ketocarbonyl compounds, α-diketones are preferably used from the viewpoint of stability. Of the α-diketones, diacetyl, benzyl and camphorquinone are preferred.

Specific examples of the component (c12) include benzoyldimethoxyphosphine oxide, benzoylethoxyphenylphosphine oxide, 2-methylbenzoyldiphenylphosphine oxide, 2,4,6-trimethylbenzoyldiphenylphosphine oxide and the like.

The component (C1) and the component (C2) may be used alone or in combination.

Illustrative examples of the peroxide (C2) (polymerization initiator) used include organic peroxides such as diacetyl peroxide, dipropyl peroxide, dibutyl peroxide, dicapryl peroxide, dilauryl peroxide, benzoyl peroxide (BPO), p,p'-dichlorobenzoyl peroxide, p,p'-dimethoxybenzoyl peroxide, p,p'-dimethylbenzoyl peroxide and p,p'-dinitrodibenzoyl peroxide; and inorganic peroxides such as ammonium persulfate, potassium persulfate, potassium chlorate, potassium bromate and potassium perphosphate. Of these, BPO is preferred.

The component (D) of the present invention is a water-soluble organic solvent. As described above, it serves to dissolve or disperse each of the above components uniformly, substitute water contained in a tooth with the component of the present invention and facilitate the formation of a coating having a thickness required to be bonded to the surface of the tooth. Preferably, the solvent used herein can dissolve the component (A) and/or the component (B) and can disperse or dissolve water as the component (F) and the component (A) and/or the component (B) uniformly or stably for a certain period. The organic solvent which can be used herein is preferably an organic solvent which can dissolve 30 wt % or more, more preferably 50 wt % or more of water at 37° C., particularly preferably a solvent which can mix with and/or dissolve water in a desired ratio. Specific examples of the organic solvent include alcohols such as methanol, ethanol and propanol; ethers such as diethoxyethane, 1,2-dimethoxyethane, tetrahydrofuran (THF) and dioxane; ketones such as acetone and methyl ethyl ketone; sulfoxides such as N,N-dimethyl sulfoxide (DMSO); and amides such as N,N-dimethylformamide (DMF). Higher alcohols such as ethylene glycol, propylene glycol and glycerol may also be used. Alcohols, acetone, THF and DMSO are particularly preferred when safety to a living body is taken into consideration.

The component (E) of the present invention is an organic acid and/or a salt thereof such as an organic sulfinic acid and/or a salt thereof or barbituric acid and/or a derivative thereof. The organic sulfinic acid or a salt thereof is sulfinic acid or an ordinary alkali metal salt, alkaline earth metal salt, amine salt or ammonium salt of sulfinic acid. When an aromatic sulfinic acid salt is used, the obtained cured product has an excellent color tone advantageously. The alkali metal salt is a lithium salt, sodium salt, potassium salt or the like. The alkaline earth metal salt is a magnesium salt, calcium salt, strontium salt, barium salt or the like. The amine salt is a primary amine salt such as methylamine, ethylamine, propylamine, butylamine, aniline, toluidine, phenylenediamine or xylylenediamine; secondary amine salt such as dimethylamine, diethylamine, dipropylamine, dibutylamine, piperidine, N-methylaniline, N-ethylaniline, diphenylamine or N-methyltoluidine; or tertiary amine such as trimethylamine, triethylamine, pyridine, N,N-dimethylaniline, N,N-di(β-hydroxyethyl)aniline, N,N-diethylamine, N,N-dimethyltoluidine, N,N-diethyltoluidine or N,N-(β-hydroxyethyl)toluidine. The ammonium salt is an ammonium salt, tetramethylammonium salt, tetraethylammonium salt, tetrapropylammonium salt or trimethylbenzylammonium salt.

Illustrative examples of the organic sulfinic acid include alkanesulfinic acids such as ethanesulfinic acid, propanesulfinic acid, hexanesulfinic acid, octanesulfinic acid, decanesulfinic acid and dodecanesulfinic acid; alicyclic sulfinic acids such as cyclohexanesulfinic acid and cyclooctanesulfinic acid; and aromatic sulfinic acids such as benzenesulfinic acid, o-toluenesulfinic acid, p-toluenesulfinic acid, ethylbenzenesulfinic acid, decylbenzenesulfinic acid, dodecylbenzenesulfinic acid, chlorobenzenesulfinic acid and naphthalenesulfinic acid.

Illustrative examples of the organic sulfinate include lithium benzenesulfinate, sodium benzenesulfinate, potassium benzenesulfinate, magnesium benzenesulfinate, calcium benzenesulfinate, strontium benzenesulfinate, barium benzenesulfinate, butylamine benzenesulfinate, aniline benzenesulfinate, toluidine benzenesulfinate, phenylenediamine benzenesulfinate, diethylamine benzenesulfinate, diphenylamine benzenesulfinate, triethylamine benzenesulfinate, ammonium benzenesulfinate, tetramethylammonium benzenesulfinate and trimethylbenzylammonium benzenesulfinate. Further, lithium o-toluenesulfinate, sodium o-toluenesulfinate, potassium o-toluenesulfinate, calcium o-toluenesulfinate, cyclohexylamine o-toluenesulfinate, aniline o-toluenesulfinate, ammonium o-toluenesulfinate, tetraethylammonium o-toluenesulfinate, lithium p-toluenesulfinate, sodium p-toluenesulfinate, potassium p-toluenesulfinate, p-toluenesulfinate acid, barium p-toluenesulfinate, ethylamine p-toluenesulfinate, toluidine p-toluenesulfinate, N-methylaniline p-toluenesulfinate, pyridine p-toluenesulfinate, ammonium p-toluenesulfinate, tetramethylammonium p-toluenesulfinate, sodium β-naphthalenesulfinate, strontium β-naphthalenesulfinate, triethylamine β-naphthalenesulfinate, N-methyltoluidine β-naphthalenesulfinate, ammonium β-naphthalenesulfinate, trimethylbenzylammonium β-naphthalenesulfinate and the like may also be used as the organic sulfinate.

The barbituric acid derivative as the component (E) is 1,3,5-trimethylbarbituric acid, 1,3,5-triethylbarbituric acid, 1,3-dimethyl-5-ethylbarbituric acid, 1,5-dimethylbarbituric acid, 1-methyl-5-ethylbarbituric acid, 1-methyl-5-propylbarbituric acid, 5-ethylbarbituric acid, 5-propylbarbituric acid, 5-butylbarbituric acid, 5-methyl-1-butylbarbituric acid, 1-benzyl-5-phenylbarbituric acid, 1-cyclohexyl-5-ethylbarbituric acid or an alkali metal salt thereof. The concentration of the barbituric acid derivative is preferably 0.1 to 10% of the whole dental adhesive.

The component (E) is preferably dissolved or dispersed alone or under conditions which show neutrality or alkalinity, or preserved separately from the components (A) and (H) so as to preserve the composition of the present invention stably for a long time. Stated more specifically, the component (E) is dissolved or dispersed in the component (B) or/and the component (D) or/and the component (F). For simplifying operation at the time of use, the component (E) can be impregnated into, adhered to or adsorbed to an applicator such as a sponge, e.g., a sponge ball or sponge piece, cotton ball, brush, DAPPEN DISH, mixing pad or spatula which is brought into contact with the composition of the present invention when the composition is used, so that it can be easily mixed with the composition naturally. Since this applicator can be used as a disposable applicator, it is effective in preventing infection during a dental treatment.

The component (F) of the present invention is water. The component (F) serves to reduce the pH of the composition of the present invention. Due to this effect, the components of the present invention can be diffused into a tooth because it dissolves hydroxyapatite contained in the smear layer in a relatively short time when it is applied to the chipped tooth. It has another effect that it dissolves the component (E) into the composition quickly. Water used herein is distilled water, ion exchange water, purified water or physiologic saline. Of these, distilled water, purified water and ion exchange water are preferred. Oxidization-reduction water prepared by electrolysis, such as strong acidic water or strong alkaline water, may also be used.

The component (G) of the present invention is an amine compound. The component (G) may be either an aliphatic amine, alicyclic amine or aromatic amine. Further, the component (G) may be either a primary amine, secondary amine or tertiary amine. The component (G) is preferably an aromatic amine, more preferably aromatic tertiary amine. Specific examples of the amine compound include aliphatic amines such as triethylamine, tripropyl amine, tributylamine, tripentylamine, trihexylamine, trioctylamine, diethylamine, dipropylamine, dibutylamine, dihexylamine, butylamine, hexylamlne, octylamine, decylamine and dodecylamine; alicyclic amines such as tricyclohexylamine, dicyclohexylamine and cyclohexylamine; aliphatic alkylaminobenzoic acids and alkyl esters and alkoxyalkyl esters thereof such as aniline, toluidine, xylidine, phenylenediamine, N,N-dimethylaniline, N,N-diethylaniline, N,N-diethanolaniline, N,N-dimethyltoluidine (DMPT), N,N-diethyltoluidine, N,N-diethanoltoluidine (DEPT), N,N-dimethyl-p-tert-butylaniline, N,N-diethyl-p-tert-butylaniline, N,N-dimethylanisidine, N,N-diethylanisidine, N,N-dimethyl-p-chloroaniline, N,N-dimethylaminoethyl (meth)acrylate, -N,N-diethylaminoethyl (meth)acrylate; aliphatic alkylaminobenzoic acid and alkyl esters or alkoxyalkyl esters thereof such as N,N-dimethylaminobenzoic acid and alkyl esters and alkoxyalkyl esters thereof, N,N-diethylaminobenzoic acid (DEABA) and alkyl esters and alkoxyalkyl esters thereof, N,N-dipropylaminobenzoic acid and alkyl esters and alkoxyalkyl esters thereof, N-isopropylaminobenzoic acid and alkyl esters and alkoxyalkyl esters thereof, and N-isopropyl-N-methylaminobenzoic acid and alkyl esters and alkoxyalkyl esters thereof; aliphatic alkylaminobenzaldehydes typified by N,N-dimethylaminobenzaldehyde (DMABAd), N,N-diethylaminobenzaldehyde, N,N-dipropylaminobenzaldehyde and N-isopropyl-N-methylaminobenzaldehyde; aliphatic alkylaminoacetylbenzenes and aliphatic alkylaminoacylbenzenes typified by N,N-dimethylaminoacetylbenzene, N,N-diethylaminoacetylbenzene, N,N-dipropylaminoacetylebenzene, N-isopropylaminoacetylbenzene and N-isopropyl-N-methylaminoacetylbenzene; and others such as N-phenylglycine (NPG), N-tolylglycine (NTG) and N,N-(3-methacryloyloxy-2-hydroxypropyl)phenyl glycine (NPG-GMA). These compounds may be used alone or in combination.

The component (H) of the present invention is a silane coupling agent. The silane coupling agent is preferably a polymerizable monomer having an alkoxysilyl group in the molecule. Illustrative examples of the polymerizable monomer having an alkoxysilyl group include vinyltriethoxysilane, vinyl-tris(2-methoxyethoxy)silane, allyltriethoxysilane, γ-(meth)acryloyloxypropyl trimethoxysilane, 2-styrylethyl trimethoxysilane, (meth)acryloyloxyethyl dimethyl(3-trimethoxysilylpropyl) ammonium chloride, 3-(N-styrylmethyl-2-aminoethylamino)propyl trimethoxysilane hydrochloride, trimethoxysilylpropyl allylamine and the like. Of these, γ-(meth)acryloyloxypropyl trimethoxysilane and 2-styrylethyl trimethoxysilane are preferred.

The above polymerizable monomers may be used alone or in combination.

The component (H) of the present invention may be used in arbitrary combination with the components (A) to (I) and (G). It may be used in combination with a composition described in JP-A 55-110171.

The component (H) is especially effective when it is applied to ceramics which contain hydroxyapatite, calcium phosphate, silica, zirconium phosphate, zirconia and alumina and/or a dental porcelain. When the component (H) is applied to the above ceramics, it may be contained in the composition of the present invention. Preferably, another treatment material composition containing the component (H) is first applied and then the composition of the present invention excluding the component (H) is applied.

The component (I) of the present invention is a 1,3,5-triazine-2,4-dithion derivative. The 1,3,5-triazine-2,4-dithion derivative is, for example, 6-(4-vinylbenzyl-n-propyl)amino-1,3,5-triazine-2,4-dithion in particular. A detailed description of this compound is provided in JP-A 64-83254. The component (I) is especially effective when it is applied to a noble metal such as gold, platinum, silver or palladium, or an alloy containing at least one of these metals. When it is applied to the above noble metals or noble metal alloys, it may be contained in the composition of the present invention. Preferably, another treatment material composition containing the component (I) is first applied and then the composition of the present invention excluding the component (I) is applied.

The component (H) of the present invention may be used in combination with the components (A) to (I). It may be used in combination with a composition described in JP-A 64-83254.

A thiouracil derivative may be used as required. For example, 6-methacryloyloxyhexyl-2-thiouracil-5-carboxylate may be used as the thiouracil derivative.

The composition of the present invention contains 1 to 70 parts by weight, preferably 3 to 50 parts by weight, more preferably 5 to 40 parts by weight of the component (A), 0.01 to 10 parts by weight, preferably 0.03 to 5 parts by weight, more preferably 0.05 to 3 parts by weight, of the component (C), 10 to 70 parts by weight, preferably 15 to 60 parts by weight, more preferably 20 to 50 parts by weight, of the component (D), 0.01 to 10 parts by weight, preferably 0.02 to 5 parts by weight, more preferably 0.03 to 3 parts by weight, of the component (E), and 1 to 60 parts by weight, preferably 3 to 50 parts by weight, more preferably 5 to 40 parts by weight, of the component (F) based on 100 parts by weight of the total of the components (A) and (C) to (F). The composition of the present invention further contains 1 to 200 parts by weight, preferably 5 to 150 parts by weight, more preferably 10 to 130 parts by weight, of the component (B), 0.01 to 20 parts by weight, preferably 0.03 to 15 parts by weight, more preferably 0.05 to 10 parts by weight, of the component (G), 0.01 to 60 parts by weight, preferably 0.05 to 50 parts by weight, more preferably 1 to 40 parts by weight, of the component (H), and 0.001 to 60 parts by weight, preferably 0.005 to 50 parts by weight, more preferably 0.01 to 30 parts by weight, of the component (I) based on 100 parts by weight of the total of the components (A) and (C) to (F).

In the present invention, a polymerization inhibitor, polymerization enhancer, pigment, polymer, filler, anti-fungus agent and bactericide may be contained in limits that do not impair the effect of the present invention, in addition to the above components (A) to (I). A compound having a water solubility of 5 wt % or more, e.g., a compound having a hydrophilic functional group or chain such as a hydroxyl group or oxyethylene chain in the molecule, may be contained as the polymerizable monomer. In this case, the water resistance of the obtained cured product may be impaired though the compound is effective in uniformly dissolving or dispersing the mixture of the present invention depending on the requirement. Therefore, the amount of the compound is preferably small, specifically, preferably 30 parts or less by weight, more preferably 15 parts or less by weight, particularly preferably 10 parts or less by weight based on 100 parts by weight of the component (A) or a mixture of the components (A) and (B).

The composition of the present invention may contain surfactant as required. The addition of a surfactant is effective in improving adhesion, especially effective in dissolving or dispersing each component of the composition stably. The surfactant may be an ionic surfactant or nonionic surfactant and is a compound having a critical micelle concentration (cmc) in water at 37° C. of 0.01 to 1.0 wt %.

When the surfactant is an ionic surfactant, it may be an anionic surfactant exemplified by aliphatic metal carboxylates such as sodium laurate, sodium stearate and sodium oleate; sulfated aliphatic metal carboxylates such as sodium dioctylsulfosuccinic acid; metal salts of higher alcohol sulfates such as sodium dodecylsulfate, sodium lauryl sulfate, sodium cetyl sulfate, sodium stearyl sulfate and sodium oleyl sulfate; metal salts of higher alkylether sulfates such as sodium lauryl ether sulfate obtained by sulfating an ethylene oxide adduct with a lauryl alcohol; metal salts of alkylbenzenesulfonic acids such as sodium dodecylbenzenesulfonic acid; metal salts of α-olefinsulfonic acids synthesized by reacting sulfuric acid with α-olefin; Igepon T obtained by reacting N-methyl taurine and oleic acid chloride; sulfosuccinic acid diesters typified by Aerosol OT; phosphoric ester salts of adducts of ethylene oxide with higher alcohol; and dithiophosphoric ester salts.

The surfactant may be a cationic surfactant exemplified by adducts of ethylene oxide with higher alkylamines such as stearylamine; amines prepared from lower amines typified by Soromine A, Sapamine A, ARCOBEL A, ARCOBEL G, and Onyxsan HSB; alkyltrimethyl ammonium salts such as lauryl trimethylammonium chloride; quaternary ammonium salts prepared from higher alkylamines typified by alkyldimethylbenzyl ammonium salts such as lauryl dimethylbenzyl ammonium chloride; Sapamine type quaternary ammonium salts such as Sapamine MS, Sapamine BCH and Catapak SN; and quaternary ammonium salts prepared from lower amines typified by pyridium salts such as Zelan AP and Velan PF, and methacryloyloxyethyl triammonium chloride (MAC) having radical polymerizability.

The surfactant may be an amphoteric surfactant exemplified by metal salts of higher alkylaminopropionic acids such as sodium laurylaminopropionate and sodium stearylaminopropionate; and betaines such as lauryl dimethylbetaine, stearyl dimethylbetaine and lauryl dihydroxyethylbetaine.

The surfactant may be a nonionic surfactant exemplified by polyethylene glycol type and polypropylene glycol type nonionic surfactants prepared by adding ethylene oxide or propylene oxide to higher alcohols such as lauryl alcohols typified by polyethylene glycol mono-p-isooctylphenyl ether and polyethylene sorbitan monolaurate, alkylphenols such as nonylphenol, fatty acids such as oleic acid and higher aliphatic amines such as stearylamine; and polyhydric alcohol type nonionic surfactants typified by polyhydric alcohols such as glycerine, pentaerythritol, sorbitol, sorbitan, sorbitan trioleate, diethanolamines such as monoethanolamine and diethanolamine and saccharides such as sugar.

Besides the above compounds, compounds described in "Skin Kaimenkasseizai nyumon" (New Handbook of Surfactants) (written by Takehiko Fujimoto, published by Sanyo Chemical Industries. Ltd.) may also be used as the surfactant.

The composition of the invention can be generally applied on the surface of a tooth in the thickness of 1 to 500 μm, preferably 3 to 100 μm, more preferably 5 to 70 μm as the coating thickness for effective bonding to the tooth surface. The thickness of the coating film may be selected according to application purpose and use and adjusted by controlling the viscosity of the composition by changing the ratio of the components of the composition, or by controlling the amount of the composition coated on the surface of the tooth, the number of times of coating or how to blow the composition with an air blow.

After an anti-fungus agent or bactericide is applied to the surface of a tooth in anticipation of an antifungal and/or bactericidal effect, the composition of the present invention can be applied. Illustrative examples of the anti-fungus agent or bactericide include compositions containing water of hydrogen peroxide and an alcohol and compositions containing sodium hypochlorite and chlorohexyne diglucon ate.

To preserve the composition of the present invention at room temperature for one year or more, a kit which satisfies the following three requirements is preferred.

(1) The components (A) and (E) should not be mixed together.
(2) The components (A) and (H) should not be mixed together.
(3) The components (C2) and (G) should not be mixed together.

Since requirements as to the period of preservation differ according to application purpose, the components of the composition of the present invention may be combined according to application purpose, taking into consideration the above requirements. However, the present invention is not limited by combinations of the components. The most preferred constitution of the present invention is a composition comprising the components (A) to (D) and (F) (the component (B) may be excluded) and a sponge impregnated with the component (E) or the components (E) and (G), or a composition comprising the components (A) to (D), (F) and (G) and/or (I) (the component (B) may be excluded) and a sponge impregnated with the component (E).

The most preferred kit is a kit comprising a single dropping bottle and a sponge or cotton ball impregnated with the component (E). The contents of the bottle are a mixture of the components (A) to (D) (the component (B) may be excluded), a mixture of the components (A) to (D) and (F) (the component (B) may be excluded), a mixture of the components (A), (B), (C1), (D), (F) and (G) (the component (B) may be excluded) or a mixture of the components (A) to (D) (the component (B) may be excluded), (F), (G) and (I).

The component to be impregnated into an applicator such as a sponge or cotton ball is the component (E) alone in the form of powders or granules, a mixture of the component (E) and other component in the form of powders or granules, or a mixture of the components (E) and (D) and/or (F).

The mixture of the components (E) and (D) and/or (F) is preferably a homogeneous solution or dispersion. The applicator is preferably impregnated with a saturation amount of this homogeneous solution.

This saturation amount is preferably equivalent to one drop of a mixture of the other components contained in the dropping bottle. Therefore, the applicator may be placed in a vessel in a state that it is immersed in the above homogeneous solution. This technique makes it possible to simplify a process for producing the kit by virtue of the improved storage stability (prevention of the change in properties of the components or the separation of a mixture) of a mixture of the other components not impregnated in the applicator, an easiness in handling at the time of a dental treatment and an increase In the freedom of selecting the components. Particularly when the component (F) is separated from a mixture of the other components and impregnated into the applicator, the storage stability is improved.

Before the composition of the present invention is applied, an etching agent or primer composition may be applied to the surface of an adherend, for example, a tooth, ceramic, metal or resin as required. The etching agent is a composition containing hydrochloric acid, citric acid, phosphoric acid, oxalic acid, EDTA and metal ions. The primer is a composition containing a polymerizable monomer having a hydroxyl group and/or acid group.

EXAMPLES

When the composition of the present invention is applied to a tooth to improve the effect of the present invention, the composition is preferably left to stand for 5 seconds or more, more preferably for 10 seconds or more, particularly preferably 30 seconds or more after application. This standing time is assumed to be a time required for the composition of the present invention to dissolve and diffuse part or all of the smear layer on the surface of a tooth and/or the substrate of the tooth. As the standing time increases, the effect of the present invention improves. When use of the composition of the present invention in the mouth is taken into consideration, however, it is preferred that the composition be left to stand for about 1 minute at most.

The following examples are provided for the purpose of further illustrating the present invention but are in no way to be taken as limiting.

(Test on Solubility to Water)

A water insoluble or hardly soluble radical polymerizable monomer corresponding to the component (B) of the present invention was added to distilled water so as to have a concentration of 5%, shaken at 37° C. for 10 minutes and left to stand for 4 hours, and the existence of phase separation was observed with the naked eye. Solubility was evaluated as 5% or less when phase separation was observed and 5% or more when the monomer was uniformly emulsified or dissolved. Thus, it was checked if the radical polymerizable monomer as the component (B) had a solubility at 37° C. of 5 wt % or less.

Preparation of Sponge Impregnated with Component (E): 1

0.05 g of sodium p-toluenesulfinic acid (p-TSNa: Shika Ikkyu of Kanto Kagaku Co., Ltd.) was pounded in a mortar for 10 minutes to form into powders, the obtained powders were placed in a 20 cc glass bottle, and 0.05 to 0.1 g of the Sponge S (8.3 mg of foamed polyurethane measuring 3 mm and 3 mm in diameter) provided as an accessory to Super Bond C & B was also placed in the bottle. The bottle was vigorously shaken for 3 minutes to bring the sponge into uniform contact with p-TSNa. The powders and the sponge were removed from the bottle separately and the sponge called "Cata-sponge" was used as it was. The amount of p-TSNa impregnated into one sponge was 0.4 mg on average.

Cata-sponges impregnated with sodium benzenesulfinate (BSNa), lithium p-toluenesulfinate (p-TSLi), sodium N-phenylglycine (NPG.Na), barbituric acid and barbital sodium were prepared in the same manner as described above.

Preparation of Sponge Impregnated with Component (E): 2

0.4 g of sodium p-toluenesulfinate-tetrahydrate of Wako Pure Chemical industries, Ltd.) was dissolved in 16 g of distilled water, 3 g of the resulting solution was charged into a 10 cc glass bottle, and 0.05 to 0.1 g of the Sponge S (8.3 mg of foamed urethane measuring 3 mm and 3 mm in diameter)provided as an accessory to Super Bond C & B was also placed in the bottle to be fully impregnated with the solution. Thus, the composition of the present invention was prepared as the sponge called "cata-sponge" which was fully impregnated with the solution at the time of use.

The amount of the solution impregnated into one sponge was about 16 mg.

(Test 1 on Adhesion to Tooth: without Etching)

A fresh front tooth of the lower jaw of a bovine, which was removed, frozen and preserved in water, was used as a tooth sample. The thawed bovine tooth was polished with water-resistant emery paper #80 under water injection and finger pressure by the ECOMET-III rotary polishing machine (of BUEHLER Co., Ltd.) so that the enamel and dentine of the tooth were exposed to obtain a flat surface. Immediately after water was removed from the polished bovine tooth with an air gun, a cellophane tape having a 4.8 mm diameter round hole for specifying an adhesion surface was put on the tooth.

Two drops (0.05 g) of the curable composition of the present invention were placed on a DAPPEN DISH and stirred quickly with a single cata-sponge for 3 to 5 seconds. A large amount (about 0.015 g) of the curable composition was applied to the area-specified tooth using the sponge and left to stand for 30 seconds. After an excessive liquid was removed with an air blow softly, the curable composition of the present invention was cured through exposure by a visible radiation illuminator (Translux CL of Kulzer Co., Ltd.) for 20 seconds. A 1 mm-thick paper sheet having a round hole of an inner diameter of 5.1 mm and a pressure-sensitive adhesive applied to its one side was placed and fixed to the cured composition of the present invention so that the specified area could be seen, a composite resin (Epic-TMPT of Sun Medical Co., Ltd.) was filled into the hole, and the hole was covered with a 50 $\mu$m-thick polyester film. This film was exposed to light by the visible radiation illuminator (Translux CL of Kulzer Co., Ltd.) for 40 seconds to cure the composite resin and removed, and an acryl bar was placed upright with META FAST (of Sun Medical Co., Ltd.) and left for 15 minutes. The sample was immersed in water at 37° C. for a whole day and a tensile test was made at a cross head speed of 2 mm/min.

(Test 2 on Adhesion to Tooth: with Etching Material)

A fresh front tooth of the lower jaw of a bovine, which was removed, frozen and preserved in water, was used as a tooth sample. The thawed bovine tooth was polished with water-resistant emery paper #80 under water injection and finger pressure by the ECOMET-III rotary polishing machine (of BUEHLER Co., Ltd.) so that the enamel and dentine of the tooth were exposed to obtain a flat surface. Immediately after water was removed from the polished bovine tooth with an air gun, an etching material was fully coated to the tooth with the Sponge S (not cata-sponge), washed with water after a predetermined time and dried with an air blow. A cellophane tape having a 4.8 mm diameter round hole for specifying an adhesion surface was put on the etching material coated surface of the tooth.

Two drops (0.05 g) of the curable composition of the present invention were placed on a DAPPEN DISH and stirred quickly with a single cata-sponge for 3 to 5 seconds. A large amount (about 0.015 g) of the curable composition was applied to the area-specified tooth using the sponge and left to stand for 30 seconds. After an excessive liquid was removed with an air blow softly, the curable composition of the present invention was cured through exposure by a visible radiation illuminator (Translux CL of Kulzer Co., Ltd.) for 20 seconds. A 1 mm-thick paper sheet having a 5.1 mm diameter round hole and a pressure-sensitive adhesive applied to its one side was placed and fixed to the cured composition of the present invention so that the specified area could be seen, a composite resin (Epic-TMPT of Sun Medical Co., Ltd.) was filled into the hole, and the hole was covered with a 50 μm-thick polyester film. This film was exposed to light by the visible radiation illuminator (Translux CL of Kulzer Co., Ltd.) for 40 seconds to cure the composite resin and removed, and an acryl bar was placed upright with META FAST (of Sun Medical Co., Ltd.) and left for 15 minutes. The sample was immersed in water at 37° C. for a whole day and a tensile test was made at a cross head speed of 2 mm/min.

(Test on Adhesion to Porcelain)

One side of a dental porcelain (Super Porcelain AAA, E3 of Noritake Co., Ltd.; 15×15×10) was polished with water-resistant emery paper #80 under water injection and finger pressure by the ECOMET-III rotary polishing machine (of BUEHLER CO., LTD.) to obtain a flat surface. 0.3 g of a phosphoric acid solution (high-viscosity Red of Sun Medical Co., Ltd.) was applied to the polished surface, left to stand for 30 seconds, fully washed with water and dried with an air blow. A cellophane tape having a 4.8 mm-diameter round hole for specifying an adhesion area was put on the phosphoric acid solution coated surface.

Bottle 1 (as defined in the examples below), bottle 2 as the curable compositions of the present invention and a cata-sponge were prepared and used. The bottle 2 was prepared by dissolving 4-MET (2.5 parts by weight) as the component (A) and γ-methacryloyloxypropyl trimethoxysilane (γ-METS; 2.5 parts by weight) as the component (H), and mixing and dissolving 95 parts by weight of MMA as the component (B). About 0.015 g of the resulting mixture was collected in 10 minutes with a syringe, applied to the area specified surface and 10 seconds after, dried with an air blow. Further, about 0.015 g of each of the mixed solutions of the bottle 1 and the cata-sponge was applied and 30 seconds after application, volatilized by an air blow until the solution on the surface became immobilized. Thereafter, the adhesive composition of the present invention was cured through exposure by a visible radiation illuminator (Translux Ch) for 20 seconds. A 1 mm-thick paper sheet having a 5.1 mm diameter round hole and an adhesive material applied to its one side was placed and fixed to the cured composition so that the specified area could be seen, a composite resin (Epic-TMPT of Sun Medical Co., Ltd.) was filled into the hole, and the hole was covered with a 50 μm-thick polyester film. This film was exposed to light by a visible radiation illuminator (Translux CL of Kulzer Co., Ltd.) for 40 seconds to cure the composite resin and removed, and an acryl bar was placed upright with META FAST (of Sun Medical Co., Ltd.) and left for 15 minutes. The sample was immersed in water at 37° C. for a whole day and a tensile test was made at a cross head speed of 2 mm/min.

(Test on Adhesion to Dental Noble Metal (Gold-silver-palladium))

The surface of a dental noble metal (gold-silver-palladium alloy; Prime Cast (of Sekifuku Kinzoku Co., Ltd.) 10×10×3 mm) was polished with water-resistant emery paper #600 under water injection and finger pressure by the ECOMET-III rotary polishing machine (of BUEHLER Co., Ltd.) to obtain a flat surface. The polished surface was treated with sandblast with $Al_2O_3$ (Sahara (of JELENKO); 50 μm aluminum oxide) at a rate of 5 kg/cm$^2$ for about 10 seconds, washed in water with ultrasonic waves and dried with an air blow. A cellophane tape having a 4.8 mm diameter round hole for specifying an adhesion area was put on the treated surface.

Bottle 1, bottle 3 as the curable compositions of the present invention and a cata-sponge were prepared. The bottle 3 was prepared by dissolving acetone (99.5 parts by weight) as the component (D) and 6-(4-vinylbenzyl-n-propyl)amino-1,3,5-triazine-2,4-dithion (VTD, 0.5 part by weight) as the component (I). About 0.015 g of the resulting mixture was collected with a syringe, applied to the area specified surface and 10 seconds after, dried with an air blow. Further, about 0.015 g of each of the mixed solutions of the bottle 1 and the cata-sponge was applied and 30 seconds after application, volatilized by an air blow until the solution on the surface became immobilized. Thereafter, the adhesive composition of the present invention was cured through exposure by a visible radiation illuminator (Translux Ch) for 20 seconds. A 1 mm-thick paper sheet having a 5.1 mm diameter round hole and an adhesive material applied to one side was placed and fixed to the cured composition so that the specified area could be seen, a composite resin (Epic-TMPT of Sun Medical Co., Ltd.) was filled into the hole, and the hole was covered with a 50 μm-thick polyester film. This film was exposed to light by a visible radiation illuminator (Translux CL of Kulzer Co., Ltd.) for 40 seconds to cure the composite resin and removed, and an acryl bar was placed upright with META FAST (of Sun Medical Co., Ltd.) and left for 15 minutes. The sample was immersed in water at 37° C. for a whole day and a tensile test was made at a cross head speed of 2 mm/min.

Example 1

Tests were conducted in accordance with the above tooth adhesion tests 1 and 2. 30 Grams of 4-META, 30 g of MMA, 30 g of 2.6E, 0.1 g of d,l-camphorquinone (CQ), 30 g of acetone and 10 g of distilled water were mixed and dissolved. This resulting solution was charged into a dropping bottle (bottle 1) and 2 drops (0.05 g) of the solution and one cata-sponge were vigorously stirred in a DAPPEN DISH for 5 seconds, and the composition of the present invention was applied to the surface of a tooth with the sponge. The composition of the present invention was applied to a dental porcelain and a noble metal in accordance with the respective adhesion test methods.

Examples 2 to 13, 16 to 25 and 27 to 30

Compositions shown in Tables 1 and 2 were prepared in the same manner as in Example 1 and applied to the surface of a tooth.

Examples 14 and 15

The procedure of Example 1 was repeated except that compositions were applied to the surface of a tooth in accordance with the tooth adhesion test 1 in the case of no etching in tables of examples. However, right before the application of the compositions of the present invention to the surface of the tooth, the Neo Cleaner (main component: sodium hypochlorite, manufactured by Neo Seiyaku Co., Ltd.) or a 2% aqueous solution of chlorohexyne digluconate was coated to the surface of the tooth for sterilization, and 30 seconds after, washed with water and dried.

The compositions were applied in accordance with the tooth adhesion test 2 in the case of etching in tables of examples. High-viscoslty Red (main component: hydrogen phosphate, manufactured by Sun Medical Co., Ltd.) was coated as an etching material and 15 seconds after, washed with water. Thereafter, the AD Gel (main component: sodium hypochlorite, manufactured by Kuraray Co., Ltd.) was coated and 60 seconds after, fully washed with water. Water on the treated surface was wiped out with a cotton ball softly and the compositions of the present invention were applied before the surface was not dried.

Example 26

The composition of the present invention consisting of bottle 1 containing components excluding water as the component (F) and a sponge impregnated with the component (E) and water was applied in the same manner as in Example 1.

Abbreviations in Tables 1 to 6 stand for the following compounds.

4-META: 4-methacryloyloxyethyl trimellitic anhydride
4-MET: 4-methacryloyloxyethyl trimellitic acid
MMA: methyl methacrylate
2,6E: condensate of 1 mole of an adduct of bisphenol A with ethylene oxide and 2 moles of methacrylic acid (number of chains (m+n≧2.6) of ethylene oxide added
CQ: d,l-camphorquinone
BEDB: n-butoxyethyl N,N-dimethylaminobenzoic acid
DMABAE: ethyl N,N-dimethylaminobenzoic acid
Bis-GMA: adduct of 1 mole of bisphenol A with 2 moles of glycidyl methacrylate
UDMA: adduct of 1 mole of 2,2,4-(or 2,4,4-)trimethyl-1,6-hexamethylene diisocyanate with 2 moles of 2-hydroxyethyl methacrylate
TBAS: 2-methyl-2-acrylamide propanesulfonic acid
5-MASA: 5-methacryloylaminosalicylic acid
4-MSA: 4-methacryloyloxysalicylic acid
5-MSA: 5-methacryloyloxysalicylic acid
HEMA: 2-hydroxyethyl methacrylate
p-TSNa: sodium p-toluenesulfinate
p-TSLi: lithium p-toluenesulfinate
BSNa: sodium benzenesulfinate
γ-METS: γ-methacryloyloxypropyl trimethoxysilane
VTD: 6-(4-vinylbenzyl-n-propyl)amino-1,3,5-triazine-2,4-dithion
CB-1: methacryloyloxyhydrogen phthalate (trade name of Shin Nakamura Kagaku Co., Ltd.)
ETOH: ethanol
TMDPO: 2,4,6-trimethylbenzoyldiphenylphosphine oxide
10-3: surface treating material Green (of Sun Medical Co., Ltd.)
EDTA: 0.3META2.Na-0.2MEDTA.Fe.Na (pH 7.4)
phosphoric acid: high-viscosity Red (of Sun medical Co., Ltd.)
AD gel: AD Gel (Kuraray Co., Ltd.)
CHCG: 2% chlorohexyne digluconate aqneons solution
BPO: benzoyl peroxide
NPG.Na: sodium N-phenylglycine
BA: barbituric acid
BANa: barbital sodium

TABLE 1

| | | | Ex. 1 | Ex. 2 | Ex. 3 | Ex. 4 |
|---|---|---|---|---|---|---|
| bottle 1 | component A | type | 4-META | 4-MET | 4-META | 4-META |
| | | quantity (g) | 30 | 30 | 30 | 30 |
| | component B | type | MMA/2.6E | MMA/2.6E | MMA/2.6E | 2.6E |
| | | quantity (g) | 30/30 | 30/30 | 30/30 | 60 |
| | component C | type | CQ | CQ | CQ | CQ |
| | | quantity (g) | 0.1 | 0.1 | 0.1 | 0.1 |
| | component D | type | acetone | acetone | acetone | acetone |
| | | quantity (g) | 30 | 30 | 30 | 30 |
| | component F | type | distilled water | distilled water | distilled water | distilled water |
| | | quantity (g) | 10 | 10 | 10 | 10 |
| | component G | type | — | — | BEDB | DMABAE |
| | | quantity (g) | — | — | 0.1 | 0.1 |
| | total quantity | (g) | 0.05 | 0.05 | 0.05 | 0.05 |
| bottle 2 (used only for porcelain) | component H | type | — | — | — | — |
| | | mixture | γ-METS/4-MET/MMA | γ-METS/4-MET/MMA | γ-METS/4-MET/MMA | γ-METS/4-MET/MMA |
| | | quantity (g) | 2.5/2.5/95 | 2.5/2.5/95 | 2.5/2.5/95 | 2.5/2.5/95 |
| bottle 3 (used only for gold-silver-palladium) | component I | type | — | — | — | — |
| | | mixture | VTD/acetone | VTD/acetone | VTD/acetone | VTD/acetone |
| | | quantity (g) | 0.5/99.5 | 0.5/99.5 | 0.5/99.5 | 0.5/99.5 |
| sponge | component E | type | p-TSNa | p-TSLi | p-TSNa | p-TSNa |
| | | quantity (mg) | 0.4 | 0.4 | 0.4 | 0.4 |
| thickness of coating film (μm) | | | 50 | — | — | — |
| adhesion strength without etching | | | | | | |
| dentine of bovine tooth | | | 5.1 | 5.0 | 5.8 | 5.1 |
| enamel of bovine tooth | | | 5.2 | 5.1 | 5.6 | 5.3 |
| etched (type, time: seconds) | | | 10–3,10 | — | 10–3,10 | — |
| dentine of bovine tooth | | | 13.1 | — | 14.8 | — |
| enamel of bovine tooth | | | 15.2 | — | 13.2 | — |
| porcelain VITA | | | 10 | 9 | 11 | 11 |
| gold-silver-palladium | | | 9 | 9 | 11 | 11 |

TABLE 2

|  |  |  | Ex. 5 | Ex. 6 | Ex. 7 | Ex. 8 |
|---|---|---|---|---|---|---|
| bottle 1 | component A | type | 4-META | 4-META | 4-META/TBAS | 4-META |
|  |  | quantity (g) | 30 | 30 | 30/5 | 30 |
|  | component B | type | MMA/2.6E | BisGMA | MMA/UDMA | MMA/UDMA |
|  |  | quantity (g) | 30/30 | 60 | 30/30 | 30/30 |
|  | component C | type | CQ | CQ | CQ | CQ |
|  |  | quantity (g) | 0.1 | 0.1 | 0.1 | 0.1 |
|  | component D | type | acetone | acetone | acetone | acetone |
|  |  | quantity (g) | 30 | 30 | 30 | 30 |
|  | component F | type | distilled water | distilled water | distilled water | distilled water |
|  |  | quantity (g) | 10 | 10 | 10 | 10 |
|  | component G | type | DMABAE | BEDB | BEDB | BEDB |
|  |  | quantity (g) | 0.1 | 0.1 | 0.1 | 0.1 |
|  |  | total quantity (g) | 0.05 | 0.05 | 0.05 | 0.05 |
| bottle 2 (used only for porcelain) | component H | type | — | — | — | — |
|  |  | mixture | γ-METS/4-MET/MMA | γ-METS/4-MET/MMA | γ-METS/4-MET/MMA | γ-METS/4-MET/MMA |
|  |  | quantity (g) | 2.5/2.5/95 | 2.5/2.5/95 | 2.5/2.5/95 | 2.5/2.5/95 |
| bottle 3 (used only for gold-silver-palladium) | component I | type | — | — | — | — |
|  |  | mixture | VTD/acetone | VTD/acetone | VTD/acetone | VTD/acetone |
|  |  | quantity (g) | 0.5/99.5 | 0.5/99.5 | 0.5/99.5 | 0.5/99.5 |
| sponge | component E | type | p-TSNa | p-TSNa | p-TSNa | p-TSNa |
|  |  | quantity (mg) | 0.4 | 0.4 | 0.4 | 0.4 |
| thickness of coating film (μm) |  |  | 50 | 60 | 40 | 40 |
| adhesion strength without etching |  |  |  |  |  |  |
| dentine of bovine tooth |  |  | 7.9 | 5.0 | 10.0 | 10.2 |
| enamel of bovine tooth |  |  | 5.6 | 5.0 | 8.9 | 5.8 |
| etched (type, time: seconds) |  |  | — | — | — | EDTA,10 |
| dentine of bovine tooth |  |  | — | — | — | 11.9 |
| enamel of bovine tooth |  |  | — | — | — | 17.1 |
| porcelain VITA |  |  | 10 | 9 | 13 | 13 |
| gold-silver-palladium |  |  | 11 | 8 | 11 | 12 |

TABLE 3

|  |  |  | Ex. 9 | Ex. 10 | Ex. 11 | Ex. 12 |
|---|---|---|---|---|---|---|
| bottle 1 | component A | type | 4-MET/S-MASA | 4-META/MA | 4-META | 4-META/4-MSA |
|  |  | quantity (g) | 25/5 | 30 | 30 | 25/5 |
|  | component B | type | MMA/2.6E | MMMA/UDMA | MMA/2.6E | MMA/2.6E |
|  |  | quantity (g) | 30/30 | 30/30 | 30/30 | 30/30 |
|  | component C | type | CQ | CQ | CQ | CQ |
|  |  | quantity (g) | 0.1 | 0.1 | 0.1 | 0.1 |
|  | component D | type | acetone | acetone | EtOH | acetone |
|  |  | quantity (g) | 30 | 30 | 30 | 30 |
|  | component F | type | distilled water | distilled water | distilled water | distilled water |
|  |  | quantity (g) | 10 | 10 | 10 | 10 |
|  | component G | type | BEDB | BEDB | DMABAE | BEDB |
|  |  | quantity (g) | 0.1 | 0.1 | 0.1 | 0.1 |
|  |  | total quantity (g) | 0.05 | 0.05 | 0.05 | 0.05 |
| bottle 2 (used only for porcelain) | component H | type | — | — | — | — |
|  |  | mixture | γ-METS/4-MET/MMA | γ-METS/4-MET/MMA | γ-METS/4-MET/MMA | γ-METS/4-MET/MMA |
|  |  | quantity (g) | 2.5/2.5/95 | 2.5/2.5/95 | 2.5/2.5/95 | 2.5/2.5/95 |
| bottle 3 (used only for gold-silver-palladium) | component I | type | — | — | — | — |
|  |  | mixture | VTD/acetone | VTD/acetone | VTD/acetone | VTD/acetone |
|  |  | quantity (g) | 0.5/99.5 | 0.5/99.5 | 0.5/99.5 | 0.5/99.5 |
| sponge | component E | type | p-TSNa | p-TSNa | p-TSNa | p-TSNa |
|  |  | quantity (mg) | 0.4 | 0.4 | 0.4 | 0.4 |

TABLE 3-continued

|  | Ex. 9 | Ex. 10 | Ex. 11 | Ex. 12 |
|---|---|---|---|---|
| thickness of coating film (μm) | — | — | — | — |
| adhesion strength without etching | | | | |
| dentine of bovine tooth | 7.5 | 5.3 | 9.1 | 6.2 |
| enamel of bovine tooth | 6.2 | 6.2 | 8.3 | 6.8 |
| etched (type, time: seconds) | — | — | — | — |
| dentine of bovine tooth | — | — | — | — |
| enamel of bovine tooth | — | — | — | — |
| porcelain VITA | 13 | 12 | 10 | 12 |
| gold-silver-palladium | 11 | 10 | 10 | 10 |

TABLE 4

|  |  |  | Ex. 13 | Ex. 14 | Ex. 15 | Ex. 16 |
|---|---|---|---|---|---|---|
| bottle 1 | component A | type | 4-META/5-MSA | 4-MESA/TBAS | 4-MET | 4-MET |
|  |  | quantity (g) | 30 | 30/5 | 30 | 30 |
|  | component B | type | MMA/UDMA | MMA/UDMA | MMA/2.6E | MMA/2.6E |
|  |  | quantity (g) | 10 | 30/30 | 30/30 | 30/30 |
|  | component C | type | CQ | CQ | CQ | CQ |
|  |  | quantity (g) | 0.1 | 0.1 | 0.1 | 0.1 |
|  | component D | type | acetone | acetone | acetone | acetone |
|  |  | quantity (g) | 30 | 30 | 30 | 30 |
|  | component F | type | distilled water | distilled water | distilled water | distilled water |
|  |  | quantity (g) | 10 | 10 | 10 | 10 |
|  | component G | type | BEDB | BEDB | BEDB | BEDB |
|  |  | quantity (g) | 0.1 | 0.1 | 0.1 | 0.1 |
|  | total quantity | (g) | 0.05 | 0.05 | 0.05 | 0.05 |
| bottle 2 (used only for porcelain) | component H | type mixture quantity (g) | γ-METS/4-MET/MMA 2.5/2.5/95 | — | — | — |
| bottle 3 (used only for gold-silver-palladium) | component I | type mixture quantity (g) | VTD/acetone 0.5/99.5 | — | — | — |
| sponge | component E | type | p-TSNa | p-TSNa | p-TSNa | p-TSNa |
|  |  | quantity (mg) | 0.4 | 0.4 | 0.4 | 0.4 |
| thickness of coating film (μm) | | | 40 | — | 40 | 60 |
| adhesion strength without etching | | | | | | |
| for anti-fungus agent bactericide | | | | Neo Cleaner | CHCG | |
| dentine of bovine tooth | | | 9.9 | 9.3 | 7.3 | 6.1 |
| enamel of bovine tooth | | | 8.9 | 8.8 | 6.1 | 5.6 |
| etched (type, time: seconds) | | | | phosphoric acid,15 AD Gel,60 | | |
| dentine of bovine tooth | | | — | 10.3 | — | — |
| enamel of bovine tooth | | | — | 14.3 | — | — |
| porcelain VITA | | | 10 | — | — | — |
| gold-silver-palladium | | | 9 | — | — | — |

TABLE 5

|  |  |  | Ex. 17 | Ex. 18 | Ex. 19 | Ex. 20 | Ex. 21 |
|---|---|---|---|---|---|---|---|
| bottle 1 | component A | type | 4-MET | 4-MET | 4-MET/MEP | 4-MET | 4-MET |
|  |  | quantity (g) | 30 | 10 | 10/3 | 10 | 30 |
|  | component B | type | 2.6E | MMA/UDMA | MMA/UDMA | MMA/UDMA | MMA/UDMA |
|  |  | quantity (g) | 60 | 7/10 | 9/9 | 9/9 | 30/30 |
|  | component C | type | CQ | CQ | CQ | CQ | TMDPO |
|  |  | quantity (g) | 0.1 | 0.1 | 0.1 | 0.1 | 0.1 |
|  | component D | type | acetone | acetone | EtOH | acetone | acetone |
|  |  | quantity (g) | 30 | 41 | 44 | 44 | 30 |
|  | component F | type | distilled water | distilled water | distilled water | distilled water | distilled water |
|  |  | quantity (g) | 10 | 32 | 29 | 29 | 10 |

TABLE 5-continued

|  |  |  | Ex. 17 | Ex. 18 | Ex. 19 | Ex. 20 | Ex. 21 |
|---|---|---|---|---|---|---|---|
|  | component G | type | DMABAE | DMABAE | BEDB | BEDB | BEDB |
|  |  | quantity (g) | 0.1 | 0.1 | 0.1 | 0.1 | 0.1 |
|  |  | total quantity (g) | 0.05 | 0.05 | 0.05 | 0.05 | 0.05 |
| bottle 2 (used only for porcelain) | component H | type mixture quantity (g) | — | — | — | — | — |
| bottle 3 (used only for gold-silver-palladium) | component I | type mixture quantity (g) | — | — | — | — | — |
| sponge | component E | type | p-TSNa | p-TSNa | p-TSNa | p-TSNa | p-TSNa |
|  |  | quantity (mg) | 0.1 | 0.4 | 0.4 | 0.4 | 0.4 |
| thickness of coating film (μm) |  |  | — | 20 | 20 | 20 | 50 |
| adhesion strength without etching |  |  |  |  |  |  |  |
| dentine of bovine tooth |  |  | 5.5 | 7.5 | 5.1 | 6.1 | 5.3 |
| enamel of bovine tooth |  |  | 5.8 | 11.9 | 5.0 | 6.4 | 6.2 |
| etched (type, time: seconds) |  |  | — | — | — | — | EDTA,10 |
| dentine of bovine tooth |  |  | — | — | — | — | 10.0 |
| enamel of bovine tooth |  |  | — | — | — | — | 10.3 |
| porcelain VITA |  |  | — | — | — | — | — |
| gold-silver-palladium |  |  | — | — | — | — | — |

TABLE 6

|  |  |  | Ex. 22 | Ex. 23 | Ex. 24 | Ex. 25 | Ex. 26 |
|---|---|---|---|---|---|---|---|
| bottle 1 | component A | type | 4-MET | 4-META/CB-1 | 4-MET/CB-1 | Phenyl-P | 4-MET |
|  |  | quantity (g) | 25/5 | 10/50 | 10/50 | 10 | 10 |
|  | component B | type | MMA/2.6E | — | — | MMA/UDMA | MMA/UDMA |
|  |  | quantity (g) | 30/30 | — | — | 30/30 | 7/10 |
|  | component C | type | TMDPO | CQ | CQ | CQ | CQ |
|  |  | quantity (g) | 0.1 | 0.1 | 0.1 | 0.1 | 0.1 |
|  | component D | type | acetone | acetone | EtOH | acetone | acetone |
|  |  | quantity (g) | 30 | 30 | 30 | 30 | 41 |
|  | component F | type | distilled water | distilled water | distilled water | distilled water | distilled water |
|  |  | quantity (g) | 10 | 10 | 10 | 10 | — |
|  | component G | type | — | — | DMABAE | TMDPO | DMABAE |
|  |  | quantity (g) | — | — | 0.1 | 1.0 | 0.1 |
|  |  | total quantity (g) | 0.05 | 0.05 | 0.05 |  |  |
| bottle 2 (used only for porcelain) | component H | type mixture quantity (g) | — | — | — | — |  |
| bottle 3 (used only for gold-silver-palladium) | component I | type mixture quantity (g) | — | — | — | — |  |
| sponge | component E | type | p-TSNa | p-TSNa | p-TSNa | p-TSNa | p-TSNa/ distilled water |
|  |  | quantity (mg) | 0.4 | 0.4 | 0.4 | 0.4 | 0.4   16 |
| thickness of coating film (μm) |  |  | 20 | 40 | — | — | — |
| adhesion strength without etching |  |  |  |  |  |  |  |
| dentine of bovine tooth |  |  | 5.1 | 5.3 | 6.1 | 9.3 | 8.0 |
| enamel of bovine tooth |  |  | 5.6 | 5.1 | 5.9 | 8.2 | 12.1 |
| etched (type, time: seconds) |  |  | — | — | — | EDTA,10 | EDTA,10 |
| dentine of bovine tooth |  |  | — | — | — | 12.6 | 11.3 |
| enamel of bovine tooth |  |  | — | — | — | 13.5 | 12.1 |
| porcelain VITA |  |  | — | — | — | 13.3 | 12.1 |
| gold-silver-palladium |  |  | — | — | — | 12.3 | 11.3 |

TABLE 7

|  |  |  | Ex. 27 | Ex. 28 | Ex. 29 | Ex. 30 |
|---|---|---|---|---|---|---|
| bottle 1 | component A | type | 4-MET | 4-MET | 4-MET | 4-MET |
|  |  | quantity (g) | 10 | 10 | 10 | 10 |
|  | component B | type | MMA/UDMA | MMA/UDMA | MMA/UDMA | MMA/UDMA |
|  |  | quantity (g) | 7/10 | 7/10 | 7/10 | 7/10 |
|  | component C | type | BPO | BPO/TMDPO | TMDPO | TMDPO |
|  |  | quantity (g) | 1.0 | 1.0/0.1 | 0.5 | 0.5 |
|  | component D | type | acetone | acetone | acetone(/HEMA) | acetone(/HEMA) |
|  |  | quantity (g) | 41 | 41 | 41/3.5 | 41/3.5 |
|  | component F | type | distilled water | distilled water | distilled water | distilled water |
|  |  | quantity (g) | 10 | 10 | 6.5 | 6.5 |
|  | component G | type | — | — | DMABAE | DMABAE |
|  |  | quantity (g) |  |  | 0.5 | 0.5 |
|  |  | total quantity (g) | — | — | — | — |
| bottle 2 (used only for porcelain) | component H | type | — | — | — | — |
|  |  | mixture quantity (g) | 0.05 | 0.05 | 0.05 | 0.05 |
| bottle 3 (used only for gold-silver-palladium) | component I | type | — | — | — | — |
|  |  | mixture quantity (g) |  |  |  |  |
| sponge | component E | type | p-TSNa/NPG-Na 0.2/0.2 | p-TSNa/NPG-Na 0.2/0.2 | BA | BANa |
|  |  | quantity (mg) |  |  | 0.4 | 0.4 |
| thickness of coating film (μm) |  |  | — | — | — | — |
| adhesion strength without etching |  |  |  |  |  |  |
| dentine of bovine tooth |  |  | — | — | 8.7 | 6.1 |
| enamel of bovine tooth |  |  | 7.8 | 6.0 | 7.7 | 6.4 |
| etched (type, time: seconds) |  |  | EDTA,10 | EDTA,10 | — | — |
| dentine of bovine tooth |  |  | 9.9 | 8.2 | — | — |
| enamel of bovine tooth |  |  | 11.3 | 10.3 | — | — |
| porcelain VITA |  |  | — | — | — | — |
| gold-silver-palladium |  |  | — | — | — | — |

By using the adhesive curable composition of the present invention and a kit containing the same, the boarding materials or the like can be firmly bonded to a tooth without a pretreatment, thereby making it possible to prevent the invasion of the tooth and to greatly reduce the time and labor of work.

What is claimed is:

1. A kit for dental adhesive comprising:
   (A) radical polymerizable monomer having an acid group in the molecule,
   (C) photosensitizer (C1), peroxide (C2), or mixture thereof,
   (D) water-soluble organic solvent,
   (E) at least one powdery or granular acid or salt selected from the group consisting of organic sulfinic acid, salt thereof, mixture of said acid and said salt thereof, barbituric acid, derivative thereof, and mixture of barbituric acid and said derivative thereof, and
   (F) water,
   wherein the powdery or granular component (E) is adheredor or adsorbed to an applicator and other components are contained in at least one vessel, whereby said other components may be brought into contact with and mixed with the component (E) adhered or adsorbed to the applicator right before use.

2. The dental adhesive kit of claim 1 which further comprises (B) a radical polymerizable monomer which has no acid group and is insoluble or hardly soluble in water.

3. The dental adhesive kit of claim 1 which further comprises (G) an amine compound.

4. The dental adhesive kit of claim 1 which further comprises (H) a silane coupling agent.

5. The dental kit of claim 1, which further comprises (I) 6-(4-vinylbenzyl-n-propyl)amino-1,3,5-triazine-2,4-dithion.

6. The dental adhesive kit of claim 1, wherein the acid group of (A) the radical polymerizable monomer having an acid group in the, molecule is at least one member selected from the group,consisting of (A-1) a carboxyl group or a carboxylic anhydride group, (A-2) a phosphoric acid group and (A-3) a sulfonic acid group.

7. The dental adhesive kit of claims 1 or 2, wherein the photosensitizer (C1) is (C11) an α-ketocarbonyl compound or (C12) an acylphosphine oxide compound.

8. The dental adhesive kit of claim 1, wherein the other components not adhered or adsorbed in the applicator are contained in one vessel.

9. The dental adhesive kit of claim 1, wherein the applicator is selected from the group consisting of a sponge, cotton and brush.

10. The dental adhesive kit of claim 1, wherein the component (A) is contained in an amount of 1 to 70 parts weight, the component (C) is contained in an amount of 0.01 to 10 parts by weight, the component (D) is contained in an amount of 10 to 70 parts by weight, the component (E) is contained in an amount of 0.01 to 10 parts by weight and the component (F) is contained in an amount of 1 to 60 parts by weight based on 100 parts by weight of the total of the components (A) and (C) to (F).

11. The dental adhesive kit of claim 3, wherein the component (G) is contained in an amount of 0.1 to 20 parts by weight based on 100 parts by weight of the total of the components (A) and (C) to (F).

12. The dental adhesive kit of claim 2, wherein the component (B) is contained in an amount of 1 to 200 parts by weight based on 100 parts by weight of the total of the components (A) and (C) to (F).

13. The dental adhesive kit of claim 4, wherein the component (H) is contained in an amount of 0.01 to 60 parts by weight based on 100 parts by weight of the total of the components (A) and (C) to (F).

14. The dental adhesive kit of claim 5, wherein the component (I) is contained in an amount of 0.001 to 60 parts by weight based on 100 parts by weight of the total of the components (A) and (C) to (F).

15. The dental kit of claim 1, which further comprises (I) 6-(4-vinylbenzyl-n-propyl)amino-1,3,5-triazine-2,4-dithion.

16. A kit for dental adhesive comprising:
 (A) radical polymerizable monomer having an acid group in the molecule,
 (C) photosensitizer (C1), peroxide (C2), or mixture thereof,
 (D) water-soluble organic solvent,
 (E) at least one powdery or granular acid or salt selected from the group consisting of organic sulfinic acid, salt thereof, mixture of said acid and said salt thereof, barbituric acid, derivative thereof, and mixture of barbituric acid and said derivative thereof, and
 (F) water,
 wherein the powdery or granular component (E) and component (C1) or component (E) and component (C2) or component (E) and components (C1) and (C2) are adsorbed or adhered to an applicator and other components are contained in at least one vessel, whereby said other components may be brought into contact with and mixed with the components adhered or absorbed to the applicator right before use.

17. The dental kit according to claim 16, further comprising (B) radical polymerizable monomer which has no acid group and is insoluble or hardly soluble in water.

18. A kit for dental adhesive comprising:
 (A) radical polyrnerizable monomer having an acid group in the molecule,
 (C) photosensitizer (C1), peroxide (C2), or mixture thereof,
 (D) water-soluble organic solvent,
 (E) at least one powdery or granular acid or salt selected from the group consisting of organic sulfinic acid, salt thereof, mixture of said acid and said salt thereof, barbituric acid, derivative thereof, and mixture of barbituric acid and said derivative thereof,
 (F) water, and,
 (G) amine compound;
 wherein the powdery or granular component (E) and component (G) or component (E), component (G) and component (C1) are adhered or adsorbed to an applicator and other components are contained in at least one vessel, whereby said other components may be brought into contact with and with the components adhered or adsorbed to the applicator right before use.

19. The dental kit according to claim 18, further comprising (B) radical polymerizable monomer which has no acid group and is insoluble or hardly soluble in water.

* * * * *